US009611227B2

(12) United States Patent
Uchida et al.

(10) Patent No.: US 9,611,227 B2
(45) Date of Patent: Apr. 4, 2017

(54) ANTITUMOR EFFECT POTENTIATOR AND ANTITUMOR AGENT

(75) Inventors: Junji Uchida, Tokushima (JP); Koyo Shudo, Hanno (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 426 days.

(21) Appl. No.: 10/548,655

(22) PCT Filed: Mar. 11, 2004

(86) PCT No.: PCT/JP2004/003189
§ 371 (c)(1),
(2), (4) Date: Sep. 13, 2005

(87) PCT Pub. No.: WO2004/081012
PCT Pub. Date: Sep. 23, 2004

(65) Prior Publication Data
US 2006/0116345 A1    Jun. 1, 2006

(30) Foreign Application Priority Data
Mar. 14, 2003  (JP) .................................. 2003-70097

(51) Int. Cl.
*A61K 31/53*   (2006.01)
*A61K 31/519*  (2006.01)
*C07D 239/553* (2006.01)

(52) U.S. Cl.
CPC ........ *C07D 239/553* (2013.01); *A61K 31/519* (2013.01); *A61K 31/53* (2013.01)

(58) Field of Classification Search
None
See application file for complete search history.

(56) References Cited

U.S. PATENT DOCUMENTS

| 5,116,600 | A | 5/1992 | Fujii et al. | |
|---|---|---|---|---|
| 5,391,738 | A * | 2/1995 | Vecchi | 544/258 |
| 2002/0045632 | A1* | 4/2002 | Chazard | 514/269 |
| 2004/0265813 | A1* | 12/2004 | Takechi et al. | 435/6 |

FOREIGN PATENT DOCUMENTS

| EP | 0 500 953 A | 9/1992 |
|---|---|---|
| EP | 0 500 953 A1 | 9/1992 |
| EP | 0 543 015 A | 5/1993 |
| EP | 0 543 015 A1 | 5/1993 |
| WO | WO 90/07334 A1 | 7/1990 |
| WO | WO 92/04028 A1 | 3/1992 |
| WO | 02/076459 A1 | 10/2002 |

OTHER PUBLICATIONS

Freshney (Culture of Animal Cells, A Manual of Basic Technique, Alan R. Liss, Inc., 1983, New York, p. 4).*
Dermer (Bio/Technology, 1994, 12:320).*
Gura (Science, v278, 1997, pp. 1041-1042).*
Chollet et al. Phase II trial with S-1 in chemotherapy-naïve patients with gastric cancer. A trial performed by the EORTC Early Clinical Studies Group. European Journal of Cancer, vol. 39, Issue 9, Jun. 2009, pp. 1264-1270.*
Gura et. al. (Science, 1997, 278:1041-1042.*
Johnson et. al. (British Journal of Cancer, 2001, 84:1424-1431).*
TS-1® capsule 20 prescription information (Taiho Pharmaceutical Co., Ltd, Aug. 2006).*
Shirasaka et al., "Development of a novel form of an oral 5-fluorouracil derivative (S-1) directed to the potentiation of the tumor selective cytotoxicity of 5-fluorouracil by two biochemical modulators", Anti-Cancer Drugs, 1996, 7, pp. 548-557.
Royce et al., "Progress in Colorectal Cancer Chemotherapy How Far Have We Come, How Far to Go?", Drugs and Aging, vol. 17, No. 3, 2000, pp. 201-216.
Brito et al., "Fluoropyrimidines. A critical evaluation," Oncology, 57(Suppl. 1), 2-8 CODEN: ONCOBS; ISSN: 0030-2414, 1999.
Ikeda et al., "Koshuyo Zai 'TS1' no Yakuri Sayo to Tainai Dotai", Antibiotics & Chemotherapy 17 (7), pp. 1318 to 1331 (2001).
Martoni et al., "Weekly Regimen of 5-FU vs 5-FU + Intermediate Dose Folinic Acid in the Treatment of Advanced Colorectal Cancer", Anticancer Research 12: 607-612, (1992).
Lin et al., "Phase II Study of Oral Tegafur-Uracil and Folinic Acid as First-line Therapy for Metastatic Colorectal Cancer: Taiwan Experience", Japanese Journal of Clinical Oncology, 2000, 30(11), pp. 510-514.
Examination report dated Aug. 6, 2013 for in Patent Application No. 900/DELNP/2009.
Isla et al., "Oral Tegafur and Folinic Acid for the Treatment of Advanced Colorectal Cancer", European Journal Of Cancer, vol. 33, No. 1, Jan. 1997, pp. 166-167.

* cited by examiner

*Primary Examiner* — Marcos Sznaidman
*Assistant Examiner* — Rayna B Rodriguez
(74) *Attorney, Agent, or Firm* — Rothwell, Figg, Ernst & Manbeck, P.C.

(57) ABSTRACT

The present invention provides an antitumor effect potentiator for enhancing antitumor activity of an antitumor agent comprising tegafur in a therapeutically effective amount, gimeracil in an amount effective for enhancing an antitumor effect, and oteracil potassium in an amount effective for inhibiting a side effect. The antitumor effect potentiator comprising at least one member selected from the group consisting of folinic acid and pharmacologically acceptable salts thereof. The present invention also provides a method for enhancing an antitumor effect of an antitumor agent comprising the step of administering to a patient the aforementioned antitumor effect potentiator; and a method for cancer treatment comprising the step of administering to a patient the aforementioned antitumor agent.

19 Claims, No Drawings

ANTITUMOR EFFECT POTENTIATOR AND ANTITUMOR AGENT

CROSS REFERENCE TO RELATED APPLICATION

This application is a 35 USC §371 National Phase Entry Application from PCT/JP2004/003189, filed Mar. 11, 2004, and designating the U.S.

TECHNICAL FIELD

The present invention relates to an antitumor effect potentiator and an antitumor agent.

BACKGROUND ART

The research and development of antitumor agents has been actively pursued. A variety of effective antitumor agents are clinically used in the treatment of malignant tumors.

For example, tegafur is a drug that is activated in vivo and releases an active form, i.e., 5-fluorouracil (hereinafter referred to as "5-FU"), and is known as an improved antitumor agent that exhibits less toxicity and side effects than 5-FU itself. Moreover, a combined drug of tegafur and uracil is known to have a greater antitumor effect than tegafur alone. In particular, a combined drug having a tegafur to uracil molar ratio of 1 to 4 is commercially available as capsules and granules (trade name: UFT, manufactured by Taiho Pharmaceutical Co., Ltd.). This combined drug exhibits significantly enhanced antitumor effect compared with tegafur alone due to the fact that uracil, which does not have any antitumor effect by itself, inhibits the inactivation of 5-FU which is promptly metabolized and inactivated in vivo.

Japanese Patent Publication No. 2557303 discloses that the antitumor effect of an antitumor agent containing a combined drug of tegafur and uracil can be markedly potentiated without an increase in toxicity when it is used in combination with folinic acid or a salt thereof.

WO90/07334 discloses that the use of oxonic acid or a salt thereof in combination with 5-FU or a 5-FU derivative can inhibit the development of inflammation that may be caused by 5-FU or the 5-FU derivative.

Japanese Patent Publication No. 2614164 discloses an antitumor effect potentiator containing as active ingredients 2,4-dihydroxy-5-chloropyridine (gimeracil) and oxonic acid or a salt thereof which can increase the antitumor effect of tegafur while inhibiting side effects. It also discloses a 3-membered antitumor agent containing tegafur, gimeracil, and oxonic acid or a salt thereof as active ingredients. In particular, a combined drug containing tegafur, gimeracil, and oteracil potassium in a molar ratio of 1:0.4:1 is commercially available as capsules (trade name: TS-1, manufactured by Taiho Pharmaceutical Co., Ltd.). This antitumor agent has an enhanced antitumor effect due to the function of gimeracil, which exhibits a 5-FU degradation inhibitory effect about 200 times greater than that of uracil. Moreover, oxonic acid and salts thereof specifically inhibit the increase in gastrointestinal toxicity that is likely to be accompanied by the antitumor effect potentiation when tegafur and gimeracil are used in combination, thereby enhancing the therapeutic effect.

However, in view of the current state of cancer treatment, development of a pharmaceutical agent with a greater antitumor effect is required in order to completely inhibit the growth of tumors so as to prolong patient survival.

DISCLOSURE OF THE INVENTION

The present invention has been accomplished in view of the state of the art described above. A primary object of the invention is to provide a novel antitumor effect potentiator that can increase the antitumor effect of an antitumor agent containing tegafur, gimeracil, and oxonic acid or a salt thereof without aggravating side effects; and a novel antitumor agent with a high antitumor effect that contains the antitumor effect potentiator.

The inventors conducted extensive research to achieve the aforementioned object, and as a result, found that the use of folinic acid or a pharmacologically acceptable salt thereof, none of which have any antitumor effect by themselves, in combination with a 3-membered antitumor agent containing tegafur, gimeracil, and oteracil potassium, can markedly enhance the antitumor effect of the antitumor agent without notably aggravating toxicity. The present invention has been accomplished based on this finding.

In particular, the present invention provides antitumor effect potentiators, antitumor agents, methods for treating cancer, and methods for enhancing an antitumor effect, etc., as described below.

1. An antitumor effect potentiator for enhancing antitumor activity of an antitumor agent comprising tegafur in a therapeutically effective amount, gimeracil in an amount effective for enhancing an antitumor effect, and oteracil potassium in an amount effective for inhibiting a side effect, the antitumor effect potentiator comprising at least one member selected from the group consisting of folinic acid and pharmacologically acceptable salts thereof in an amount effective for enhancing an antitumor effect.

2. The antitumor effect potentiator according to Item 1, wherein the antitumor agent comprises tegafur, gimeracil, and oteracil potassium in a tegafur:gimeracil:oteracil potassium molar ratio of 1:0.4:1.

3. An antitumor agent comprising, as active ingredients, tegafur in a therapeutically effective amount, gimeracil in an amount effective for enhancing an antitumor effect, oteracil potassium in an amount effective for inhibiting a side effect, and at least one member selected from the group consisting of folinic acid and pharmacologically acceptable salts thereof in an amount effective for enhancing an antitumor effect.

4. The antitumor agent according to Item 3, wherein the antitumor agent is in a pharmaceutical preparation form comprising two or more separate preparations each of which contains one of the active ingredients consisting of tegafur, gimeracil, oteracil potassium, and at least one member selected from the group consisting of folinic acid and pharmacologically acceptable salts thereof, or two or more of the active ingredients in any combination, or in a pharmaceutical preparation form comprising a single preparation which contains all of the active ingredients.

5. The antitumor agent according to Item 3, wherein the amount of the active ingredients is such that, per mol of tegafur, gimeracil is in an amount of 0.1 to 5 mol, oteracil potassium is in an amount of 0.1 to 5 mol, and the at least one member selected from the group consisting of folinic acid and pharmacologically acceptable salts thereof is in an amount of 0.01 to 10 mol.

6. The antitumor agent according to Item 5, wherein the active ingredients are contained in a molar ratio of tegafur:gimeracil:oteracil potassium: the at least one member selected from the group consisting of folinic acid and pharmacologically acceptable salts thereof=1:0.4:1:0.01 to 10.

7. The antitumor agent according to Item 3, wherein the antitumor agent is in a pharmaceutical preparation form comprising a combined preparation comprising 3 ingredients, i.e., tegafur, gimeracil and oteracil potassium, as active ingredients, and a pharmaceutical preparation comprising the at least one member selected from the group consisting of folinic acid and pharmacologically acceptable salts thereof as an active ingredient.

8. A kit comprising a combination of pharmaceutical compositions for treating cancer in a mammal comprising:
    (a) an antitumor composition comprising tegafur in a therapeutically effective amount, gimeracil in an amount effective for enhancing an antitumor effect, and oteracil potassium in an amount effective for inhibiting a side effect, and
    (b) a composition comprising at least one member selected from the group consisting of folinic acid and pharmacologically acceptable salts thereof in an amount effective for enhancing an antitumor effect of the antitumor composition.

9. A method for treating cancer in a mammal comprising the step of administering to the mammal tegafur in a therapeutically effective amount, gimeracil in an amount effective for enhancing an antitumor effect, oteracil potassium in an amount effective for inhibiting a side effect, and at least one member selected from the group consisting of folinic acid and pharmacologically acceptable salts thereof in an amount effective for enhancing an antitumor effect.

10. A method for enhancing an antitumor effect when administering to a mammal an antitumor agent comprising tegafur in a therapeutically effective amount, gimeracil in an amount effective for enhancing an antitumor effect, and oteracil potassium in an amount effective for inhibiting a side effect,
    the method comprising the step of administering to a patient at least one member selected from the group consisting of folinic acid and pharmacologically acceptable salts thereof in an amount effective for enhancing the antitumor effect.

11. The method according to Item 10, wherein the at least one member selected from the group consisting of folinic acid and pharmacologically acceptable salts thereof in an amount effective for enhancing an antitumor effect is administered to the patient concurrently with, or within 4 hours before or after, the administration of the antitumor agent comprising tegafur in a therapeutically effective amount, gimeracil in an amount effective for enhancing an antitumor effect, and oteracil potassium in an amount effective for inhibiting a side effect.

12. Use of at least one member selected from the group consisting of folinic acid and pharmacologically acceptable salts thereof to produce an antitumor effect potentiator for enhancing an antitumor effect of an antitumor agent comprising tegafur in a therapeutically effective amount, gimeracil in an amount effective for enhancing an antitumor effect, and oteracil potassium in an amount effective for inhibiting a side effect.

13. Use of at least one member selected from the group consisting of folinic acid and pharmacologically acceptable salts thereof to produce an antitumor agent with an enhanced antitumor effect that comprises tegafur in a therapeutically effective amount, gimeracil in an amount effective for enhancing an antitumor effect, and oteracil potassium in an amount effective for inhibiting a side effect.

The antitumor effect potentiator of the present invention contains at least one member selected from the group consisting of folinic acid and pharmacologically acceptable salts thereof as an active ingredient. Due to the administration of antitumor effect potentiator, the antitumor effect of an antitumor agent containing 3 ingredients, i.e., tegafur, gimeracil and oteracil potassium, as active ingredients can be significantly enhanced.

Folinic acid used as an active ingredient of the antitumor effect potentiator is a known compound and has been used as a toxicity reducing agent for folic acid antagonists. Folinic acid does not exhibit an antitumor effect by itself. There are two optical isomers of folinic acid, i.e., the d-isomer and the l-isomer. In the preset invention, the d-isomer and the l-isomer as well as a mixture of the d-isomer and the l-isomer are usable. In particular, it is preferable to use the l-isomer or a mixture of the d-isomer and the l-isomer. An example of pharmacologically acceptable salt of folinic acid is the calcium salt.

Tegafur (5-fluoro-1-(2-tetrahydrofuryl)-2,4-(1H, 3H)-pyrimidinedione), an active ingredient of the antitumor agent, is a known compound, and is a drug activated in vivo and releases the active form, i.e., 5-FU. Tegafur can be produced according to known methods, for example, the method disclosed in Japanese Examined Patent Publication No. 1974-10510.

Gimeracil (2,4-dihydroxy-5-chloropyridine) is also a known compound, and although it does not exhibit any antitumor activity by itself, it can markedly potentiate an antitumor effect by inhibiting the in vivo metabolic inactivation of 5-FU.

Oteracil potassium (monopotassium 1,2,3,4-tetrahydro-2,4-dioxo-1,3,5-triazine-6-carboxylate) is also a known compound. Although it does not exhibit any antitumor activity by itself, it mostly distributes in the gastrointestinal tract and inhibits the activation of 5-FU at that location, thereby preventing gastrointestinal toxicity caused by 5-FU.

With respect to the antitumor agent containing 3 ingredients, i.e., tegafur, gimeracil and oteracil potassium, as active ingredients, the amount of each active ingredient may be within the ranges described in connection with known combined drugs, for example, that disclosed in Japanese Patent Publication No. 2614164. It is usually such that, per mole of tegafur, gimeracil is used in an amount of about 0.1 to about 5 mol and preferably about 0.1 to about 1.5 mol, and oteracil potassium in about 0.1 to about 5 mol and preferably about 0.2 to about 2 mol. A particularly preferable molar ratio of the 3 ingredients is tegafur:gimeracil:oteracil potassium=1:0.4:1.

The antitumor agent containing 3 ingredients, i.e., tegafur, gimeracil and oteracil potassium, as active ingredients may be prepared in a pharmaceutical preparation form comprising two or more separate pharmaceutical preparations each of which contains one of the active ingredients or two or more of the active ingredients in any combination, or in a pharmaceutical preparation form comprising a single pharmaceutical preparation containing all of these active ingredients. In any case, such antitumor agents are prepared as pharmaceutical compositions according to standard methods using suitable pharmaceutical carriers. Carriers usable herein are those that are commonly used for known drugs, for example, excipients, binders, disintegrators, lubricants, colorants, taste enhancers, flavor enhancers, surfactants, etc.

When an antitumor agent in a pharmaceutical preparation form comprising two or more separate pharmaceutical preparations as described above is used, each pharmaceutical preparation may be administered concurrently, or one pharmaceutical agent may be administered any time before or after the administration of the other pharmaceutical preparation(s). Preferably, all of the pharmaceutical preparations are administered concurrently, or one pharmaceutical preparation is administered within 4 hours, and more preferably within 2 hours, before or after the administration of the other pharmaceutical preparation(s).

The antitumor effect potentiator comprising at least one member selected from the group consisting of folinic acid and pharmacologically acceptable salts thereof as an active ingredient of the present invention may be independently prepared in various kinds of unit dosage form. In this case, the antitumor effect potentiator is prepared as a pharmaceutical preparation according to standard methods using suitable pharmaceutical carriers. Carriers usable herein are those that are commonly used for known drugs, for example, excipients, binders, disintegrators, lubricants, colorants, taste enhancers, flavor enhancers, surfactants, etc. The antitumor effect potentiator prepared in various kinds of unit dosage form may be administered concurrently with or separately from the antitumor agent containing 3 ingredients, i.e., tegafur, gimeracil and oteracil potassium, as active ingredients that may also be prepared in various kinds of unit dosage form. That is, the antitumor effect potentiator of the present invention can be administered any time before or after or concurrently with the administration of the antitumor agent containing 3 ingredients, i.e., tegafur, gimeracil and oteracil potassium, as active ingredients. Preferably, the antitumor effect potentiator is administered concurrently with or within 4 hours before or after the administration of the antitumor agent, and more preferably within 2 hours, before or after the administration of the antitumor agent.

When the antitumor effect potentiator of the present invention is administered concurrently with, or before or after, the administration of the aforementioned antitumor agent containing 3 ingredients, i.e., tegafur, gimeracil and oteracil potassium, as active ingredients, the antitumor effect potentiator is preferably administered in an amount such that the amount of the at least one member selected from the group consisting of folinic acid and pharmacologically acceptable salts thereof, per mol of tegafur, is within the range of about 0.01 to about 10 mol, preferably about 0.05 to about 5 mol, and more preferably about 0.1 to about 2 mol.

According to the present invention, an antitumor agent containing an antitumor effect potentiator can be prepared, in which at least one member selected from the group consisting of folinic acid and pharmacologically acceptable salts thereof, i.e., an active ingredient of the aforementioned antitumor effect potentiator, is concomitantly present with an antitumor agent containing 3 ingredients, i.e., tegafur, gimeracil and oteracil potassium, as active ingredients. In this case, the antitumor agent may be in a combined pharmaceutical preparation form comprising a single pharmaceutical preparation containing all the active ingredients, i.e., tegafur, gimeracil and oteracil potassium, and at least one member selected from the group consisting of folinic acid and pharmacologically acceptable salts thereof; or in a pharmaceutical preparation form comprising two or more separate preparations each of which contains one of the active ingredients or two or more of the active ingredients in any combination. In particular, the antitumor agent is preferably in a separate pharmaceutical preparation form comprising a combined preparation containing 3 ingredients, i.e., tegafur, gimeracil and oteracil potassium, as active ingredients and a pharmaceutical preparation containing at least one member selected from the group consisting of folinic acid and pharmacologically acceptable salts thereof as an active ingredient.

The aforementioned antitumor agent containing at least one member selected from the group consisting of folinic acid and pharmacologically acceptable salts thereof can be prepared in any unit dosage form for administration. It may be prepared as a pharmaceutical preparation according to known methods using suitable pharmaceutical carriers. Carriers usable herein are those that are heretofore used for known drugs, for example, excipients, binders, disintegrators, lubricants, colorants, taste enhancers, flavor enhancers, surfactants, etc.

With respect to the antitumor agent, the amounts of the ingredients are not limited. Usually, per mol of tegafur, gimeracil is in an amount of about 0.1 to about 5 mol and preferably about 0.1 to about 1.5 mol, oteracil potassium is in about 0.1 to about 5 mol and preferably about 0.2 to about 2 mol, and the at least one member selected from the group consisting of folinic acid and pharmacologically acceptable salts thereof is in about 0.01 to about 10 mol, preferably about 0.05 to about 5 mol and more preferably about 0.1 to about 2 mol. In particular, a preferable molar ratio of the ingredients is tegafur gimeracil:oteracil potassium: the at least one member selected from the group consisting of folinic acid and pharmacologically acceptable salts thereof=about 1:0.4:1:0.01 to 10, more preferably about 1:0.4:1:0.05 to 5, and particularly preferably about 1:0.4:1:0.1 to 2. When the antitumor agent is in a separate pharmaceutical preparation form in which a combined pharmaceutical preparation containing 3 ingredients, i.e., tegafur, gimeracil and oteracil potassium, as active ingredients and a pharmaceutical preparation containing at least one member selected from the group consisting of folinic acid and pharmacologically acceptable salts thereof as an active ingredient are separately present as described above, the antitumor agent preferably contains the combined pharmaceutical preparation containing tegafur, gimeracil, and oteracil potassium in a molar ratio of 1:0.4:1, and the pharmaceutical preparation containing the at least one member selected from the group consisting of folinic acid and pharmacologically acceptable salts thereof in an amount of about 0.01 to about 10 mol, preferably about 0.05 to about 5 mol, and more preferably about 0.1 to about 2 mol, per mol of tegafur.

According to the present invention, the antitumor effect potentiator and the combined agent containing tegafur, gimeracil, and oteracil potassium described above are applicable to a kit comprising a combination of pharmaceutical compositions for mammalian cancer treatment comprising:

(a) an antitumor composition containing tegafur in a therapeutically effective amount, gimeracil in an amount effective for enhancing an antitumor effect, and oteracil potassium in an amount effective for inhibiting a side effect, and (b) a composition containing at least one member selected from the group consisting of folinic acid and pharmacologically acceptable salts thereof in an amount effective for enhancing the antitumor effect of the antitumor composition. The compositions contained in such a kit may be in any known pharmaceutical preparation forms. The compositions are usually kept in any commonly used containers according to their pharmaceutical preparation form.

Such a kit is applicable to, for example, a kit for treatment of mammalian (including human) cancer that contains at least the 4 ingredients:
(i) tegafur in a therapeutically effective amount,
(ii) gimeracil in an amount effective for enhancing an antitumor effect,
(iii) oteracil potassium in an amount effective for inhibiting a side effect, these all being part of an antitumor composition, and
(iv) at least one member selected from the group consisting of folinic acid and pharmacologically acceptable salts thereof in an amount effective for enhancing the antitumor effect of the antitumor composition, and that also contains at least 2 containers for keeping these ingredients, in which tegafur and the at least one member selected from the group consisting of folinic acid and pharmacologically acceptable salts thereof are kept in separate containers.

Unit dosage forms usable in administering the antitumor effect potentiator and antitumor agent of the present invention to treat malignant tumors of mammals, including humans, are not limited, and can be selected according to the purpose of the treatment. Specific examples are injections, suppositories, ophthalmic solutions, ointments, aerosols, and like parenteral forms; and tablets, coated tablets, powders, granules, capsules, fluids, pills, suspensions, emulsions, and like oral forms. The antitumor effect potentiator and the antitumor agent can be produced in such dosage forms according to methods heretofore known in this technical field.

In preparing solid oral agents, such as tablets, powders, and granules, for example, the following can be used as carriers: lactose, saccharose, sodium chloride, glucose, urea, starch, calcium carbonate, kaolin, crystalline cellulose, silicic acid, methylcellulose, glycerol, sodium alginate, gum arabic, and like excipients; simple syrups, liquid glucose, liquid starch, gelatin solutions, polyvinyl alcohol, polyvinyl ether, polyvinylpyrrolidone, carboxymethylcellulose, shellac, methylcellulose, ethylcellulose, water, ethanol, potassium phosphate, and like binders; dried starch, sodium alginate, powdered agar, powdered laminaran, sodium hydrogencarbonate, calcium carbonate, polyoxyethylene sorbitan fatty acid esters, sodium lauryl sulfate, stearic acid monoglycerides, starch, lactose, and like disintegrators; saccharose, stearic acid, cocoa butter, hydrogenated oils, and like disintegration inhibitors; quaternary ammonium salts, sodium lauryl sulfate, and like absorption enhancers; glycerol, starch, and like humectants; starch, lactose, kaolin, bentonite, colloidal silicic acid, and like adsorbents; purified talc, stearic acid salts, powdered boric acid, polyethylene glycol, and like lubricants; etc. Furthermore, if necessary, tablets may be provided with a standard coating, for example, as sugar-coated tablets, gelatin-coated tablets, enteric-coated tablets, film-coated tablets, double-layer tablets, multi-layer tablets, and the like.

In preparing pills, glucose, lactose, starch, cacao butter, hydrogenated vegetable oils, kaolin, talc, and like excipients; powdered gum arabic, powdered tragacanth, gelatin, and like binders; laminaran, agar, and like disintegants; etc., can be used as carriers.

Capsules can be prepared by mixing the antitumor effect potentiator or the combined agent containing tegafur, gimeracil and oteracil potassium as well as the potentiator with the aforementioned various carriers and filling hard gelatin capsules, soft capsules or the like, with the mixture.

In preparing suppositories, polyethylene glycol, cacao butter, lanolin, higher alcohols, esters of higher alcohols, gelatin, semisynthetic glycerides, Witepsol (registered trademark, Dynamite Nobel Inc.), etc., can be used as carriers.

In preparing injections, water, ethyl alcohol, macrogol, propylene glycol, ethoxylated isostearyl alcohol, polyoxylated isostearyl alcohol, polyoxyethylene sorbitan fatty acid esters, and like diluents; sodium citrate, sodium acetate, sodium phosphate, and like pH-adjusters and buffers; sodium pyrosulfite, EDTA, thioglycolic acid, thiolactic acid, and like stabilizers; etc., can be used as carriers. In such cases, NaCl, glucose, or glycerol may be used in the pharmaceutical preparation in amounts sufficient to prepare an isotonic solution. Moreover, standard auxiliary dissolvents, soothing agents, topical anesthetics, etc., may be used. Subcutaneous, intramuscular, and intravenous injections can be prepared according to standard methods in conjunction with such carriers.

Liquid preparations may take the form of water-based or oil-based suspensions, solutions, syrups, or elixirs, and can be prepared according to standard methods using heretofore used additives.

In preparing the pharmaceutical preparation in the form of ointments such as pastes, creams, and gels, for example, white petrolatum, paraffin, glycerol, cellulose derivatives, polyethylene glycol, silicon, bentonite, etc., can be used as diluents.

The amount of the at least one member selected from the group consisting of folinic acid and pharmacologically acceptable salts thereof, which is an active ingredient of the antitumor effect potentiator of the present invention, and the amounts of tegafur, gimeracil, oteracil potassium, and the at least one member selected from the group consisting of folinic acid and pharmacologically acceptable salts thereof, which are active ingredients of the antitumor agent of the present invention, vary according to the dosage form, route of administration, dosing schedule, etc., and are not limited, and hence can be suitably selected. It is usually preferable that the active ingredients account for about 1 to about 70 wt. % of the pharmaceutical preparation.

The route of administration of the antitumor effect potentiator and the antitumor agent of the present invention are not limited and include, for instance, enteral administration, oral administration, rectal administration, intraoral administration, transdermal administration, etc. They can be determined according to the form of pharmaceutical preparation, the age, sex, and condition of the patient, and other factors. For example, tablets, pills, solutions, suspensions, emulsions, granules, capsules, and the like are administered orally; suppositories are administered intrarectally; and ointments are applied to the skin, the mucous membranes of the mouth, etc.

The dosage of each active ingredient in the present invention can be suitably selected according to the method of administration, the age, sex and other factors of the patient, the degree of the disease, etc. In oral administration, it is preferable to use the following ranges as a rough standard: the amount of tegafur is about 0.1 to about 100 mg/kg/day, preferably about 0.5 to about 30 mg/kg/day, and more preferably about 0.8 to about 20 mg/kg/day; the amount of gimeracil is about 0.05 to about 100 mg/kg/day, preferably about 0.1 to about 50 mg/kg/day, and more preferably about 0.2 to about 5 mg/kg/day; the amount of oteracil potassium is about 0.1 to about 100 mg/kg/day, preferably about 0.5 to about 40 mg/kg/day, and more preferably about 0.7 to about 20 mg/kg/day; and the amount of the at least one member selected from the group consisting of folinic acid and pharmacologically acceptable salts thereof, calculated as the amount of folinic acid, is about 0.05 to about 1000 mg/kg/day, preferably about 0.1 to about 100 mg/kg/day, and more preferably about 0.2 to about 10 mg/kg/day.

The antitumor effect potentiator and the antitumor agent of the present invention can be administered in a single dose or in 2 to 4 divided doses per day. When in the form of an injectable solution for, for example, an intravenous injection, the antitumor effect potentiator and the antitumor agent, which if necessary may be diluted with a physiological saline or injectable glucose solution, can be gradually administered to an adult over 5 minutes or longer, usually in an amount corresponding to about 0.5 to about 50 mg/kg/day of tegafur. When in the form of a suppository, the antitumor effect potentiator and the antitumor agent are administered to an adult once or twice a day at an interval of 6 to 12 hours usually in an amount corresponding to about 0.5 to about 100 mg/kg/day of tegafur by insertion into the rectum.

The types of malignant tumors treatable by the administration of the pharmaceutical preparation of the present invention are not limited, insofar as the active form, i.e., 5-fluorouracil, is reactive thereto; for example, head and neck cancers, stomach cancer, colon/rectal cancer (cancer of the large intestine), liver cancer, gallbladder/biliary cancer, pancreatic cancer, lung cancer, breast cancer, vesical cancer, prostatic cancer, uterine cancer, pharyngeal cancer, esophageal cancer, renal cancer, ovarian cancer, etc. In particular, a remarkable effect can be expected toward colon/rectal cancer (cancer of the large intestine), breast cancer, esophageal cancer, stomach cancer, head and neck cancers, and lung cancer.

ously implanted on the backs of male nude mice BALB/c-nu/nu. When the average tumor volume (=major axis (mm)×minor axis $(mm)^2$) reached about 200 $mm^3$, the mice were divided into groups.

The following preparations each dissolved or suspended in a 0.5% hydroxypropylmethyl cellulose (HPMC) solution were orally administered to the mice once a day in amounts as shown in Table 1 for 9 consecutive days from the day after grouping: calcium folinate; a tegafur/gimeracil/oteracil potassium combined drug (molar ratio of tegafur:gimeracil:oteracil potassium=1:0.4:1); a combined drug containing the tegafur/gimeracil/oteracil potassium combined drug described above and calcium folinate; a tegafur/uracil combined drug (molar ratio of tegafur:uracil=1:4); and a combined drug containing the tegafur/uracil combined drug described above and calcium folinate.

The ratio of the tumor volume 10 days after grouping to the tumor volume upon grouping was calculated to obtain a relative tumor volume. The tumor growth inhibition ratio (%) was determined using the relative tumor volumes of the drug-administered groups and the control group.

The body weight change was calculated by subtracting the body weight of mice 10 days after the beginning of administration from the body weight of mice upon grouping and used as a parameter of whole-body toxicity of the pharmaceutical preparation. The results thus obtained are presented in Table 1. Although calcium folinate was used in the experiment, the dosage given in the table is that calculated as the amount of folinic acid.

TABLE 1

| Drug | Dosage (mg/kg/day) | Dosage of folinic acid (mg/kg/day) | Relative tumor volume (Mean ± SD) | Tumor growth inhibition ratio (%) | Body weight change (g) |
| --- | --- | --- | --- | --- | --- |
| none | 0 | 0 | 2.38 | — | −0.5 |
| none | 0 | 20.0 | 2.24 | 6.1 | −0.8 |
| Tegafur + gimeracil + oteracil potassium | 8.3 + 2.4 + 8.1 | 0 | 1.76* | 26.1 | −1.7 |
| Tegafur + gimeracil + oteracil potassium | 8.3 + 2.4 + 8.1 | 20.0 | 1.35*# | 43.3 | −3.1 |
| Tegafur + uracil | 20.0 + 44.8 | 0 | 1.91* | 19.7 | −1.1 |
| Tegafur + uracil | 20.0 + 44.8 | 20.0 | 1.83* | 23.3 | −2.6 |

*$p < 0.05$, compared with the control group (the group not given any drug)
$p < 0.05$, compared with the group given tegafur/gimeracil/oteracil potassium only According to the present invention, the antitumor effect of an antitumor agent containing 3 ingredients, i.e., tegafur, gimeracil and oteracil potassium, as active ingredients can be significantly strengthened without notably increasing toxicity, such as gastrointestinal toxicity, due to the use of a composition containing at least one member selected from the group consisting of folinic acid and pharmacologically acceptable salts thereof as an antitumor effect potentiator.

BEST MODE FOR CARRYING OUT THE INVENTION

Examples are given below to illustrate the invention in more detail.

Example 1

A cubic fragment measuring about 2 mm in diameter of the human colon cancer cell line KM20C was subcutane-

Example 2

A cubic fragment measuring about 2 mm in diameter of the human colon cancer cell line Colon 38 was subcutaneously implanted on the backs of male mice C57BL/6. When the average tumor volume (=major axis (mm)×minor axis $(mm)^2$) reached about 150 $mm^3$, the mice were divided into groups.

The following preparations each dissolved or suspended in a 0.5% hydroxypropylmethyl cellulose (HPMC) solution were orally administered to the mice once a day in amounts as shown in Table 2 for 9 consecutive days from the day after grouping: calcium folinate; a tegafur/gimeracil/oteracil potassium combined drug (molar ratio of tegafur:gimeracil:oteracil potassium=1:0.4:1); a combined drug containing the tegafur/gimeracil/oteracil potassium combined drug described above and calcium folinate; a tegafur/uracil combined drug (molar ratio of tegafur:uracil=1:4); and a combined drug containing the tegafur/uracil combined drug described above and calcium folinate.

The ratio of the tumor volume 12 days after grouping to the tumor volume upon grouping was calculated to obtain a relative tumor volume. The tumor growth inhibition ratio (%) was determined using the relative tumor volumes of the drug-administered groups and the control group.

The body weight change was calculated by subtracting the body weight of mice 10 days after the beginning of administration from the body weight of mice upon grouping and used as a parameter of whole-body toxicity of the pharmaceutical preparation. The results thus obtained are presented in Table 2. Although calcium folinate was used in the experiment, the dosage given in the table is that calculated as the amount of folinic acid.

ously implanted on the backs of male nude mice (BALB/cA-nu). When the average tumor volume (=major axis (mm)×minor axis (mm)$^2$) reached about 200 mm$^3$, the mice were divided into groups.

A combined drug containing a tegafur/gimeracil/oteracil potassium combined drug (molar ratio of tegafur:gimeracil:oteracil potassium=1:0.4:1) and calcium folinate, dissolved or suspended in a 0.5% hydroxypropylmethyl cellulose (HPMC) solution was orally administered to the mice once a day in amounts as shown in Table 3 for 14 consecutive days from the day after grouping.

TABLE 2

| Drug | Dosage (mg/kg/day) | Dosage of folinic acid (mg/kg/day) | Relative tumor volume (Mean ± SD) | Tumor growth inhibition ratio (%) | Body weight change (g) |
|---|---|---|---|---|---|
| None | 0 | 0 | 9.49 | — | 0.4 |
| None | 0 | 40.0 | 8.78 | 7.5 | 0.7 |
| Tegafur + gimeracil + oteracil potassium | 8.7 + 2.5 + 8.5 | 0 | 1.52* | 84.0 | 0.9 |
| Tegafur + gimeracil + oteracil potassium | 8.7 + 2.5 + 8.5 | 40.0 | 0.86*# | 91.0 | 0.7 |
| Tegafur + uracil | 15.1 + 33.8 | 0 | 2.60* | 72.6 | 0.7 |
| Tegafur + uracil | 15.1 + 33.8 | 40.0 | 2.34*# | 75.3 | 0.6 |

*$p < 0.05$, compared with the control group (the group not given any drug)

$p < 0.05$, compared with the groups given either tegafur/gimeracil/oteracil potassium or tegafur/uracil As is clear from Tables 1 and 2, the use of a tegafur/gimeracil/oteracil potassium combined drug in combination with calcium folinate can significantly enhance antitumor activity without substantially aggravating toxicity compared with the use of the tegafur/gimeracil/oteracil potassium combined pharmaceutical preparation alone. Moreover, this enhanced antitumor effect is substantially greater than that of the use of a tegafur/uracil combined drug in combination with calcium folinate.

Example 3

A cubic fragment measuring about 2 mm in diameter of the human colon cancer cell line KM20C was subcutane- The ratio of the tumor volume 15 days after grouping to the tumor volume upon grouping was calculated to obtain a relative tumor volume. The tumor growth inhibition ratio (%) was determined using the relative tumor volumes of the drug-administered groups and the control group.

The body weight change was calculated by subtracting the body weight of mice 15 days after the beginning of administration from the body weight of mice upon grouping used as a parameter of whole-body toxicity of the pharmaceutical preparation. The results thus obtained are presented in Table 3. Although calcium folinate was used in the experiment, the dosage given in the table is that calculated as the amount of folinic acid.

TABLE 3

| Drug | Dosage (mg/kg/day) | Dosage of folinic acid (mg/kg/day) | Relative tumor volume (Mean ± SD) | Tumor growth inhibition ratio (%) | Body weight change (g) |
|---|---|---|---|---|---|
| None | 0 | 0 | 4.75 ± 0.69 | — | −0.3 |
| None | 0 | 20.0 | 4.50 ± 1.25 | 5.4 | −0.6 |
| Tegafur + gimeracil + oteracil potassium | 5.7 + 1.7 + 5.6 | 0 | 3.48 ± 0.35* | 26.9 | −1.8 |
| Tegafur + gimeracil + oteracil potassium | 5.7 + 1.7 + 5.6 | 2.5 | 3.31 ± 0.38* | 30.5 | −1.1 |
| Tegafur + gimeracil + oteracil potassium | 5.7 + 1.7 + 5.6 | 5.0 | 2.85 ± 0.30*# | 40.0 | −2.3 |
| Tegafur + gimeracil + oteracil potassium | 5.7 + 1.7 + 5.6 | 10.0 | 2.61 ± 0.28*# | 45.0 | −2.2 |
| Tegafur + gimeracil + oteracil potassium | 5.7 + 1.7 + 5.6 | 20.0 | 2.55 ± 0.25*# | 46.4 | −1.8 |

*$p < 0.01$, compared with the control group (the group not given any drug)
$p < 0.01$, compared with the group given tegafur/gimeracil/oteracil potassium only The results of the investigation of the effect of calcium folinate dosage in enhancement of the antitumor effect of the tegafur/gimeracil/oteracil potassium combined drug using the human colon cancer cell line KM20C show some enhancement even at the dose of 2.5 mg/kg/day, and a clear enhancement at the dose of 5 mg/kg/day.

Formulation examples of the antimumor effect potentiator and the antitumor agent of the present invention are given below.

Formulation Example 1

| Folinic acid | 100 mg |
|---|---|
| Lactose | 170 mg |
| Crystalline cellulose | 77 mg |
| Magnesium stearate | 3 mg |
| Amount per capsule | 350 mg |

Capsules were prepared according to a standard method using the formulation presented above.

FORMULATION EXAMPLE 2

| Calcium folinate | 200 mg |
|---|---|
| Lactose | 340 mg |
| Cornstarch | 450 mg |
| Hydroxypropylmethyl cellulose | 10 mg |
| Granules | 1000 mg |

Granules were prepared according to a standard method using the formulation presented above.

Formulation Example 3

| Calcium folinate | 500 mg |
|---|---|
| Lactose | 240 mg |
| Cornstarch | 250 mg |
| Hydroxypropylmethyl cellulose | 10 mg |
| Powders | 1000 mg |

Powders were prepared according to a standard method using the formulation presented above.

Formulation Example 4

| Folinic acid | 50 mg |
|---|---|
| Lactose | 90 mg |
| Crystalline cellulose | 30 mg |
| Magnesium stearate | 2 mg |
| Talc | 3 mg |
| Hydroxypropylmethyl cellulose | 10 mg |
| Amount per tablet | 185 mg |

Tablets were prepared according to a standard method using the formulation presented above.

Formulation Example 5

| Calcium folinate | 200 mg |
|---|---|
| Distilled water for injection | Suitable amount |
| Amount per ampule | 5 ml |

Injectable solutions were prepared according to a standard method using the formulation presented above.

Formulation Example 6

| Tegafur | 50 mg |
|---|---|
| Gimeracil | 14.5 mg |
| Oteracil potassium | 49 mg |
| Folinic acid | 250 mg |
| Lactose | 280 mg |
| Corn starch | 298 mg |
| Hydroxypropylmethyl cellulose | 10 mg |
| Amount per wrapper | 951.5 mg |

Granules were prepared according to a standard method using the formulation presented above.

Formulation Example 7

| Tegafur | 25 mg |
|---|---|
| Gimeracil | 7.25 mg |
| Oteracil potassium | 24.5 mg |
| Folinic acid | 75 mg |
| Lactose | 51 mg |
| Crystalline cellulose | 28 mg |
| Magnesium stearate | 5 mg |
| Amount per capsule | 215.75 mg |

Capsules were prepared according to a standard method using the formulation presented above.

Formulation Example 8

| Tegafur | 20 mg |
|---|---|
| Gimeracil | 5.8 mg |
| Oteracil potassium | 19.6 mg |
| Folinic acid | 51 mg |
| Lactose | 51 mg |
| Crystalline cellulose | 15 mg |
| Magnesium stearate | 3 mg |
| Cornstarch | 14 mg |
| Hydroxypropylmethyl cellulose | 10 mg |
| Amount per tablet | 190.4 mg |

Tablets were prepared according to a standard method using the formulation presented above.

Formulation Example 9

| Tegafur | 200 mg |
|---|---|
| Gimeracil | 58 mg |
| Oteracil potassium | 196 mg |
| Folinic acid | 512 mg |
| Witepsol W-35 | 1034 mg |
| Amount per suppository | 2000 mg |

Suppositories were prepared according to a standard method using the formulation presented above.

The invention claimed is:

1. A pharmaceutical composition comprising tegafur, gimeracil, oteracil potassium and calcium folinate, wherein the molar ratio of tegafur:gimeracil:oteracil potassium is 1:0.4:1 and calcium folinate is in an amount of 0.1 to 2 mol, per mol of tegafur.

2. A pharmaceutical kit comprising two or more separate preparations each of which contains at least one of the active ingredients consisting of tegafur, gimeracil, oteracil potassium, and calcium folinate wherein when said two or more separate preparations are combined, the molar ratio of tegafur:gimeracil:oteracil potassium is 1:0.4:1 and calcium folinate is in an amount of 0.1 to 2 mol, per mol of tegafur.

3. The pharmaceutical kit according to claim 2, wherein one preparation comprises a combined preparation of tegafur, gimeracil and oteracil potassium, and in a separate preparation, calcium folinate.

4. A kit comprising a combination of pharmaceutical compositions for treating cancer in a mammal comprising:
(a) a composition comprising tegafur, gimeracil, and oteracil potassium in a tegafur:gimeracil:oteracil potassium molar ratio of 1:0.4:1, and
(b) a composition comprising calcium folinate in an amount of 0.1 to 2 mole per mole of tegafur.

5. A pharmaceutical kit comprising two or more separate dosage forms each of which contains at least one of the active ingredients consisting of tegafur, gimeracil, oteracil potassium, and calcium folinate, wherein when said two or more separate dosage forms are combined, the molar ratio of tegafur:gimeracil:oteracil potassium is 1:0.4:1 and calcium folinate is in an amount of 0.1 to 2 mol, per mol of tegafur, and wherein said separate dosage forms are in the same container.

6. The pharmaceutical kit according to claim 5, wherein one dosage form comprises a combined preparation of tegafur, gimeracil and oteracil potassium, and a separate dosage form comprises calcium folinate.

7. The pharmaceutical composition according to claim 1, further comprising a pharmaceutically acceptable carrier.

8. The pharmaceutical composition according to claim 7, where said pharmaceutically acceptable carrier is selected from the group consisting of excipients, binders, disintegrators, lubricants, colorants, taste enhancers, flavor enhancers, and surfactants.

9. The pharmaceutical kit according to claim 2, wherein said separate preparations are separate solid dosage forms suitable for oral administration.

10. The kit according to claim 9, wherein said separate solid dosage forms are packaged in a single container.

11. The kit according to claim 9, wherein said solid dosage forms are tablets or capsules.

12. The kit according to claim 11, wherein said tablets are coated tablets.

13. The kit according to claim 9, wherein said solid dosage forms are selected from the group consisting of tablets, coated tablets, powders, granules, capsules, and pills.

14. The pharmaceutical kit according to claim 2, wherein said separate preparations are in a dosage form selected from the group consisting of injections, suppositories, ophthalmic solutions, ointments, aerosols, tablets, powders, granules, capsules, fluids, pills, suspensions, and emulsions.

15. The pharmaceutical composition according to claim 1, further comprising a carrier suitable for enteral administration, oral administration, rectal administration, intraoral administration or transdermal administration.

16. The pharmaceutical composition according to claim 1, wherein said composition is packaged as a single dose or as 2-4 divided doses to be administered per day.

17. The pharmaceutical composition according to claim 16, wherein said single dose or 2-4 divided doses results in the administration of 0.1 to 100mg/kg/day of Tegafur, 0.05 to 100 mg/kg/day of gimeracil, 0.1 to 100 mg/kg/day of oteracil potassium and 0.05 to 1000 mg/kg/day of folinic acid administered as calcium folinate.

18. The pharmaceutical composition according to claim 17, wherein said single dose or 2-4 divided doses results in the administration of 0.5 to 30 mg/kg/day of Tegafur, 0.1 to 50 mg/kg/day of gimeracil, 0.5 to 40 mg/kg/day of oteracil potassium and 0.1 to 100 mg/kg/day of folinic acid administered as calcium folinate.

19. The pharmaceutical composition according to claim 18, wherein said single dose or 2-4 divided doses results in the administration of 0.8 to 20 mg/kg/day of Tegafur, 0.2 to 5 mg/kg/day of gimeracil, 0.7 to 20 mg/kg/day of oteracil potassium and 0.2 to 10 mg/kg/day of folinic acid administered as calcium folinate.

* * * * *